United States Patent
Xiao et al.

(12) 
(10) Patent No.: US 6,607,720 B1
(45) Date of Patent: Aug. 19, 2003

(54) GENETICALLY ALTERED MAMMALIAN EMBRYONIC STEM CELLS, THEIR LIVING PROGENY, AND THEIR THERAPEUTIC APPLICATION FOR IMPROVING CARDIAC FUNCTION AFTER MYOCARDIAL INFARCTION

(76) Inventors: Yong-Fu Xiao, 26 Paquot Rd., Wayland, MA (US) 01778; James P. Morgan, 56 Norwood Ave., Newton Centre, MA (US) 02459

( * ) Notice: Subject to any disclaimer, the term of this patent is extended or adjusted under 35 U.S.C. 154(b) by 0 days.

(21) Appl. No.: 09/684,679

(22) Filed: Oct. 7, 2000

Related U.S. Application Data

(63) Continuation-in-part of application No. 09/655,124, filed on Sep. 5, 2000.

(51) Int. Cl.[7] .................... A01N 63/00; A01N 43/04; A61K 48/00; A61K 31/70; C12N 15/00
(52) U.S. Cl. ............... 424/93.21; 514/44; 435/325; 435/377; 435/455
(58) Field of Search .................. 536/23.1; 435/325, 435/455, 377; 800/8; 424/93.21; 514/44

(56) References Cited

U.S. PATENT DOCUMENTS

| | | | |
|---|---|---|---|
| 5,639,618 A | 6/1997 | Gay | 435/7.21 |
| 5,843,780 A | 12/1998 | Thomson | 435/363 |
| 6,146,888 A | 11/2000 | Smith et al. | 435/325 |
| 6,200,806 B1 | 3/2001 | Thomson | 435/366 |
| 6,280,718 B1 | 8/2001 | Kaufman et al. | 424/93.1 |

OTHER PUBLICATIONS

Klug, M.G. et al. Genetically Selected Cardiomyocytes from Differentiating Embryonic Stem cells Form Stable Intracardiac Grafts. J. Clin. Invest. vol. 98:216–224, 1996.*
Lewis, B.S. et al. Angiogenesis by Gene Therapy: A new horizon for myocardial revascularization? Cardiovascular Res. 35:490–497, 1997.*
Sinnaeve, P. et al. Gene Therapy in the cardiovascular system: an update. Cardiovascular Res. 44:498–506, 1999.*
Inverardi, L. et al. Cell Transplantation. Transplantation Biology, Chapter 56, 1996, pp. 679–687.*
Verma, I.M. et al. Gene Therapy—Promises, problems and prospects. Nature, 389:239–242, 1997.*
Makrides, S.C. Components of Vectors for Gene Transfer and Expression in Mammalian Cells. Protein Expression and Purification, 17:183–202, 1999.*
Zink, D. et al. Mammalian Genome Organization and its Implications for the Development of Gene Therapy Vectors. Gene Therapy and Molecular Biology, 6:1–24, 2001.*
Ioffe et al., WW6: An embroyonic stem cell line with an inert genetic marker that can be traced in chimeras, Aug. 1995, Proc. Natl. Acad. Sci., vol. 92, pp. 7357–7361.*
Odorico et al., Stem Cells 19:193–204 (2001).
Schuldiner et al., PNAS 97:11307–11312 (2000).
"Stem Cells: A Primer", National Institutes of health, May 2000.
Chapter 3, "The Human Embryoic Stem Cell And The Human Embryonic Germ Cell", in Stem Cells, National Institutes of Health, 2000.
Appendix C:"Human Embryonic Stem Cells And Human Embryonic Germ Cells", in Stem Cells, National Institute of Health, 2000.
"NIH Human Embryonic Stem Cell Registry", National Institutes of Health, 2001.

* cited by examiner

Primary Examiner—Deborah Crouch
Assistant Examiner—Thai-An N. Ton
(74) Attorney, Agent, or Firm—David Prashker

(57) ABSTRACT

The present invention provides genetically altered mammalian embryonic stem cells, their living descendent progeny having an altered genomic DNA, and therapeutic methods using these cells for improving cardiac function in a living subject after myocardial infarction. The genetically altered embryonic stem and progenitor cells may be maintained in-vitro as a stable cell line; and transplanted as active, mitotic cells to an infarcted area of the myocardial using any surgical procedure. After transplantation at a chosen anatomic site within the heart of the subject, these genetically altered cells will differentiate in-site, cause a regeneration of myocardocytes, and will effect a marked improvement in cardiac function for the subject.

5 Claims, 6 Drawing Sheets

A

B

C

D

A  B

GENETICALLY ALTERED MAMMALIAN EMBRYONIC STEM CELLS, THEIR LIVING PROGENY, AND THEIR THERAPEUTIC APPLICATION FOR IMPROVING CARDIAC FUNCTION AFTER MYOCARDIAL INFARCTION

CROSS REFERENCE

This application is a Continuation-In-Part of U.S. patent application Ser. No. 09/655,124 filed Sep. 5, 2000, now pending.

FIELD OF THE INVENTION

The present invention is concerned generally with cellular compositions and methods for improving cardiac function in a living subject after the occurrence of a myocardial infarction; And is focused in particular upon the preparation and therapeutic use of novel genetically altered mammalian embryonic stem cells and their direct descendent progeny as cells for in-vivo transplantation into the infarcted areas of the myocardium in a living host subject.

BACKGROUND OF THE INVENTION

Myocardial Infarction

Myocardial infarction (MI) is a life-threatening event and may cause cardiac sudden death or heart failure. Despite considerable advances in the diagnosis and treatment of heart disease, cardiac dysfunction after MI is still the major cardiovascular disorder that is increasing in incidence, prevalence, and overall mortality (Eriksson et al., 1995). After acute myocardial infarction, the damaged cardiomyocytes are gradually replaced by fibroid nonfunctional tissue. Ventricular remodeling results in wall thinning and loss of regional contractile function. The ventricular dysfunction is primarily due to a massive loss of cardiomyocytes. It is widely accepted that adult cardiomyocytes have little regenerative capability. Therefore, the loss of cardiac myocytes after MI is irreversible. Each year more than half million Americans die of heart failure. The relative shortage of donor hearts forces researchers and clinicians to establish new approaches for treatment of cardiac dysfunction in MI and heart failure patients.

Cell Transplantation

Cell transplantation has emerged as a potential novel approach for regeneration of damaged myocardium in recent several years. Transplanted cardiomyocytes have been shown to survive, proliferate, and connect with the host myocardium (Soonpaa et al., 1994). Engrafted cells may regenerate new cardiomyocytes to replace infarcted myocardium or serve as a source for therapeutic gene transfer to infarct areas (Leor et al., 1997). Li and his coworkers (Li et al., 1996) demonstrated that transplanted fetal cardiomyocytes could form new cardiac tissue within the myocardial scar induced by cryoinjury and significantly improve heart function (Li et al. 1997). Bishop et al. (Bishop et al., 1990) reported that embryonic myocardium of rats could be implanted or cultured. They suggested that the engrafted embryonic cardiomyocytes proliferated and differentiated in host myocardium. In a recent review, Hescheler et al. (Hescheler et al., 1997) pointed out that pluripotent ES cells cultivated within embryonic bodies reproduce highly specialized phenotypes of cardiac tissue. Most of the biological and pharmacological properties of cardiac-specific ion currents were expressed in cardiomyocytes developed in vitro from pluripotent ES cells. Electrophysiological characteristics of these cells developed from ES cells were similar to those previously described in adult cardiomyocytes or neonatal mammalian heart cells (Kilborn et al., 1990; Hescheler et al., 1997).

Transplantation of xenogeneic, allogeneic, and autologous cardiomyocytes, skeletal muscle cells, and smooth muscle cells in normal and injured myocardium has been reported in different species. Several studies have demonstrated the feasibility of engrafting exogenous cells into host myocardium, including fetal cardiomyocytes (Soonpaa et al., 1994), cardiomyocytes derived from artial tumor (AT1) (Koh et al., 1993), satellite cells (Chiu et al., 1995), or bone marrow cells (Tomita et al., 1999). These engrafted cells have been histologically identified in normal myocardium up to 4 months after transplantation (Koh et al., 1993). Cells transplanted close to native cardiomyocytes could form intercalated disks. Gap junctions have been found between the engrafted fetal cardiomyocytes and the host myocardium (Soonpaa et al., 1994), thereby raising the possibility of an electrical-contraction coupling between transplanted cells and the host tissue. Recently, cell transplantation has been extended into chemically damaged myocardium in rats with coronary artery occlusion (Scorsin et al., 1996; 2000), or in cryoinjured rats (Li et al., 1996) and dogs (Chiu et al., 1995). More recently, Li and his coworkers (Li et al., 2000) showed that autologous porcine heart cell transplantation improved regional perfusion and global ventricular function after a myocardial infarction. Angiogenesis has been found after cardiomyocyte transplantation, which increases the survival of the donor cells in infarcted myocardium. Tissue engineering is a potential therapy for end-stage organ disease and tissue loss (Kim and Vacanti, 1999). Therefore, ES cell implantation is possible a novel approach for therapy of cardiac dysfunction in myocardial infarct hearts.

Over the last two decades, the morbidity and mortality of heart failure has markedly increased (Tavazzi, 1998). Therefore, finding an effective therapeutic method is one of the greatest challenges in public health for this century. Although there are several alternative ways for treatment of heart failure, such as coronary artery bypass grafting and whole-heart transplantation, myocardial fibrosis and organ shortage, along with strict eligibility criteria, mandate the search for new approaches to treat the disease. Cell transplantation has emerged to be able to increase the number of contractile myocytes in damaged hearts. Cardiomyocytes derived from embryonic stem (ES) cells may be a viable source for donor cardiomyocytes (Robbins et al., 1992). ES cells are pluripotent cells derived from the early embryo and retain the ability to differentiate into all cell types in vitro including cardiac myocytes (Maltsev et al., 1993; Metzger et al., 1994; Lavranos et al., 1995; Rathjen et al., 1998). Cardiac myocytes derived from cultured ES cells exhibit cell morphology, sarcomere formation, and cell-cell junctions similar to those observed in cardiomyocytes developing in vivo (Klug et al., 1996; Westfall et al., 1997).

In addition, by using porcine as the host, Van Meter and his colleges (Van Meter et al., 1995) showed that either transplanted human atrial cardiomyocytes or fetal human ventricular cardiomyocytes can induce the growth of new blood vessels in the graft area and the host ventricle. The increase in microcirculation could provide the grafted cells with blood supplies and remove cellular debris after cardiac injury.

Significance

After intramyocardial transplantation, these cells may communicate with their surrounding tissue, signaling the formation of blood vessels to nourish them. These transplanted cells also can differentiate to new functional cardiomyocytes in the infarct area. Therefore, it is in theory perhaps possible that such engrafted cells might restore cardiac function. One more advantage of ES cell transplantation is that less immunorejection reaction may occur because of lack of membrane surface antigens in ES cells. Thus, this unique approach might provide for an effective in-vivo therapy of myocardial infarction and heart failure. If such an unexpected approach were developed and brought into functional existence, the public health benefits of this therapeutic approach would be potentially great, because millions of patients in the world die of MI and heart failure every year.

SUMMARY OF THE INVENTION

The present invention has multiple aspects. A first aspect provides a genetically altered embryonic stem cell suitable for on-demand implantation in-vivo into a living host subject, said genetically altered embryonic stem cell comprising:

a primordial embryonic stem cell of mammalian origin which
- (i) remains uncommitted and undifferentiated while passaged in-vitro as a self-renewing cell,
- (ii) is implantable in-vivo at a chosen anatomic site as an uncommitted cell,
- (iii) integrates in-situ after implantation into the body of the living host subject at a local anatomic site, and
- (iv) differentiates in-situ after integration into a recognised type of differentiated cell of embryonic cell origin; and at least one extra nucleotide segment comprising a vector and not less than one DNA sequence encoding a specific product which is to be expressed subsequently by said embryonic stem cell in-situ.

As second aspect of the invention provides the living progeny of a genetically altered embryonic stem cell suitable for on-demand implantation in-vivo into a living host subject, said living progeny comprising:

multipotent descendant cells of mammalian embryonic stem cells origin which
- (i) remain undifferentiated while passaged in-vitro as mitotic cells,
- (ii) are implantable in-vivo at a chosen anatomic site as undifferentiated cells,
- (iii) integrate in-situ after implantation into the body of the living host subject at a local anatomic site, and
- (iv) differentiate in-situ after integration into a recognised type of differentiated cell of embryonic cell origin; and altered mammalian genomic DNA comprising a vector and not less than one DNA sequence encoding a specific product which is to be expressed subsequently by said progeny cells in-situ.

BRIEF DESCRIPTION OF THE FIGURES

The present invention may be more easily understood and better appreciated when taken in conjunction with the accompanying drawing, in which.

DETAILED DESCRIPTION OF THE INVENTION

Figure 1:
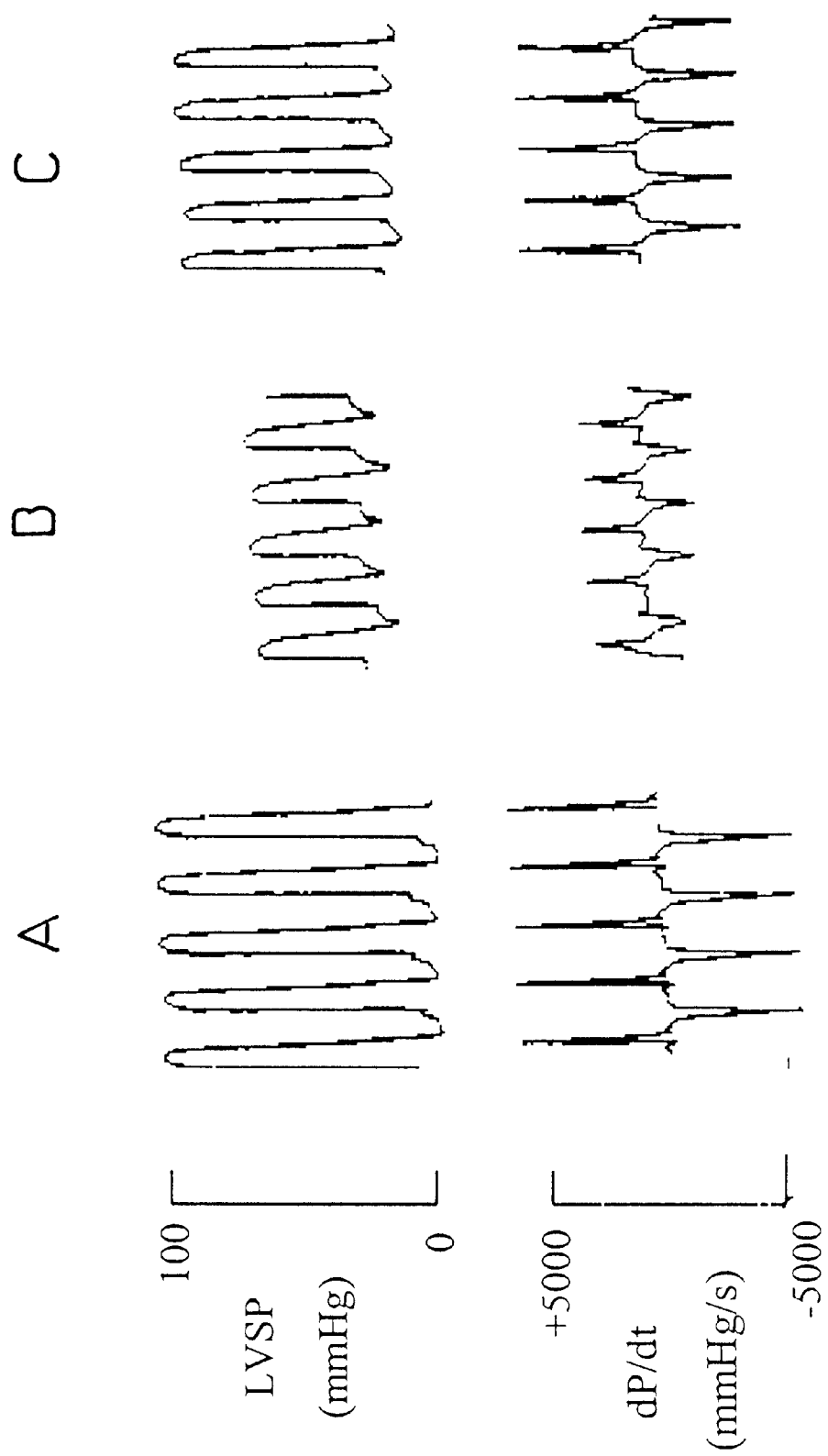
FIG. 1 is a representation of continuous chart strip recordings of hemodynamic measurements in anesthetized animals illustrating improvement of left ventricle function after ES cell transplantation.

The present invention is the preparation and therapeutic use of genetically altered, mammalian embryonic stem cells and their direct descendent progeny, embryonic progenitor cells, having an altered mammalian genomic DNA content. Embryonic stem cells and their living progeny are typically cultured in-vitro as a stable cell line; and may be passaged through many generations as a clone of active and mitotic cells having in common a single ancestor embryonic stem cell. The origin and initial source of these cultured cells is mammalian; and thus includes human as well as the well recognised murine, porcine, and other mammalian familes, species, and genera.

The present invention also requires and demands that the mammalian embryonic stem cells and their descendent progeny be genetically modified in identifiable degree such that the native genomic DNA also now comprises at least one extra nucleotide segment comprising a vector (of any conventionally known type) and not less than one additional DNA sequence encoding a specific product which is expressed by the altered stem and progenitor cells subsequently in-situ after the cells have been transplanted to a chosen anatomic site in the body of the host subject. The additional DNA sequence may be an endogeneous nucleotide segment such that the encoded specific product becomes overexpressed by the altered cell. Alternatively, the additional DNA sequence may be an exogenous nucleotide segment by which a foreign or heterologous gene becomes genetically introduced to and becomes subsequently expressed by the altered cell. Also, the extra nucleotide segment may comprises promotor, suppressor, or other regulatory genes rather than constitute a structure gene as such.

Accordingly, by the very requirements of the present invention it is thus important, if not essential, that the user be at least familiar with the many techniques for manipulating and modifying nucleotides and DNA fragments which have been reported and are today widespread in use and application. Merely exemplifying the many authoritative texts and published articles presently available in the literature regarding genes, DNA nucleotide manipulation and the expression of proteins from manipulated DNA fragments are the following: *Gene Probes for Bacteria* (Macario and De Marcario, editors) Academic Press Inc., 1990; *Genetic Analysis, Principles Scope and Objectives* by John R. S. Ficham, Blackwell Science Ltd., 1994; *Recombinant DNA*

*Methodology II* (Ray Wu, editor), Academic Press, 1995; *Molecular Cloning, A Laboratory Manual* (Maniatis, Fritsch, and Sambrook, editors), Cold Spring Harbor Laboratory, 1982; *PCR (Polymerase Chain Reaction)*, (Newton and Graham, editors), Bios Scientific Publishers, 1994; and the many references individually cited within each of these publications. All of these published texts are expressly incorporated by reference herein.

In addition, a number of issued U.S. Patents and published patent applications have been issued which describe much of the underlying DNA technology and many of the conventional recombinant practices and techniques for preparing DNA sequences coding for compounds such as VEGF. Merely exemplifying some of the relevant patent literature for this subject are: U.S. Pat. Nos. 5,486,599; 5,422,243; 5,654,273; 4,356,270; 4,331,901; 4,273,875; 4,304,863; 4,419,450; 4,362,867; 4,403,036; 4,363,877; as well as Publications Nos. W09534316-A1; W09412162-A1; W09305167-A1; W09012033-A1; W09500633; W09412162; and R09012033. All of these patent literature publications are also expressly incorporated by reference herein.

The Embryonic Stem Cell

The true source or origins of the embryonic stem cells does not meaningfully matter when used as the host recipient for transfection. All that is required for practicing the present invention is that a plurality of embryonic stem cells, with or without their decendant progeny, be available as host cells for transfection purposes.

It is both preferred and desirable that the host embryonic stem cells be a stable culture of cells maintained in-vitro; be a pure culture of cells having a common cell ancestor; and be in a active or mitotic stage of existence. It is also foreseen that the best biological compatability including histocompatibility antigens and the like exist. Thus embryonic stem cells of human origin are preferred for use with human subjects; murine sources of embryonic stem cells are desirable for used with rats and mice; and other sources of embryonic stem cells from the various mammalian species (pigs, horses, cows) are preferred for use with each of these mammalian types specifically.

When transfecting the host cells, it is very desirable that both the true embryonic stem cell as well as the direct progency decendants of these cells be transfected in common. In this manner, a single clone of true stem cells and their immediate decendants then carry the newly introduced DNA; and these genetically modified cells will individually differentiate in time to provide the desired therapeutic effect and outcome.

Embryonic stem cells have several distinctive and characteristic features, by which they are typically identified and distinguished from other kinds of cells. Embryonic stem cells are: (i) uncommitted and undifferentiated cells; (ii) pluripotent cells having an unlimited proliferation capacity; and (iii) are able to self-renew and self-maintain their existence when replicating by producing two daughter progeny cells, one of which becomes a self-renewed stem cell and the other becoming a direct and true descendent cell, usually designated a "progenitor" cell. The daughter self-renewed stem cell is identical to and indistinguishable from its parent stem cell. However, the daughter "progenitor" is markedly different from the parent stem cell.

In comparison to its parent, the descendent progenitor cell has a large but limited proliferation capacity. This direct descendent daughter cell is itself a multipotent cell which is and remains uncommitted and undifferentiated as such. However, the rate of proliferation for the daughter progenitor cell is much greater than its stem cell parent; and the progenitor cell proliferates rapidly in-situ during its finite number of reproductive cycles.

The dominant characteristic property and attribute of the progenitor cells is their ability to become committed to a single cell lineage and line of development. It is thus at the stage of commitment that the multipotency aspect and capacity of the ancestor cells becomes lost forever; and that these descendant progeny cells, and progenitor cells, become influenced in-situ by external stimuli and chemical agents in the local environment such that an irreversible commitment is made to one cell lineage and one cell embodiment type.

Once cell lineage commitment occurs in the progenitor cell progeny, the development of the cells continues within carefully controlled and selected pathway limits. Also, cell differentiation as such occurs only after a prior commitment to a set cell lineage has been made. At these latter stages of cell development, the particular form and phenotypic properties of the cell are decided; and a completely differentiated cell subsequently emerges as the full and final embodiment in the progression of events. The nature of the influencing signals and chemical molecules which act to determine cell lineage or cell fate are presently virtually unknown.

The embryonic stem cells and their progeny cells, the progenitor cells, are the host cells which are genetically altered, modified and/or changed by the intentional introduction (transfection or transduction) of specific nucleotide sequences and prepared nucleotide segments comprising endogenous or exogenous DNA encoding one or more genes to be subsequently expressed in-situ.

Endogeneous and Foreign Gene Expression

Gene therapy paradigms, especially for mycardial diseases and myocardial infarction in particular, require that the embryonic stem cell of choice be capable of either (i) overexpression of naturally existing or endogeneous genes which have been introduced to the stem cell via transfection; and/or (ii) expression of foreign or exogeneous (heterologous) genes which are not a naturally occurring or constitutive part of the genome carried by the native embryonic stem cell. For purposes of the present invention, whether the gene introduced to the host embryonic stem cell is an endogenous gene (native DNA) or is a foreign gene (exogenous DNA) does not matter, so long as the newly introduced DNA from any source is subsequently expressed by the host embryonic stem cell in measurable quantities.

As a working example and illustration, and as the present best mode of practicing the invention as whole, the overexpression of VEGF by the transfected embryonic stem cell as a consequence of introducing phVEGF$_{165}$ [as described by the experiments and evidenced by the resulting empirical data presented hereinafter] serves as a direct demonstration and probative evidence of the broad scope and applicability of the present invention.

In addition, merely as an examplary and representative (but non-exhaustive) illustration, a listing of some different growth factors and various proteins for which cDNAs are conventionally known and commonly prepared is given below. The cDNAs of these various growth factors and proteins may be inserted in an appropriate vector and then used to transfect the mammalian embryonic stem cells and progenitor cells using procedures and techniques which are also well established in this art. The transfected cells, now genetically altered with any of all of these examplary cDNAs, will express the specific product encoded by the cDNA in-situ after transplantation.

| \multicolumn{2}{c}{cDNAs of following growth factors and proteins will be used for transfection in embryonic stem cells} |  |
|---|---|
| Abbreviation | Full name |
| VEGF | Vascular endothelial growth factor |
| $FGF_{1,2}$ | Fibroblast growth factor 1 and 2 |
| TGF-$\alpha$ & $\beta_{1-5}$ | Transforming growth factor $\alpha$ & $\beta$1–5 |
| IGF-1 & -2 | Insulin-like growth factor 1 & 2 |
| SERCA I & II | Sarco/endoplasmic reticulum $Ca^{2+}$ ATPase I & II |
| $\beta_2$ | Beta adrenergic receptor II |
| Gs-protein | Stimulatory guanosine-binding protein |
| $Ca^{2+}$ channel | Calcium channel |
| Telomerase | Telomerase |

Manufacture of the Prepared DNA Sequence Fragment

It is expected and intended that the conventionally known and commonly used recombinant DNA materials, procedures, and instrumentation will be employed for the manufacture of the prepared DNA sequence fragments. Thus, the entire prepared DNA sequence structure may be synthesized directly from individual bases using the commercially available instruments and techniques. Alternatively, the DNA sequences existing in naturally occurring proteins may be replicated; and the cDNA isolated from individual clones using the appropriate enzymes and protocols. Regardless of the methods and means of manufacture, any and al of these protocols, procedures, systems, or instruments which will yield the prepared DNA sequence as an discrete fragment is suitable and appropriate for use with the present invention.

EXPERIMENTAL DESIGN AND PROCEDURES

Methods and Materials

1. Culture of embryonic stem cells

Figure 6:
FIGS. 6A and 6B are microscopic views (×200) of ES cells undergoing differentiation in culture 2 days and 8 days after withdrawal of leukemia inhibitory factor (LIF) from the conditioned culture medium.
Figure 6:
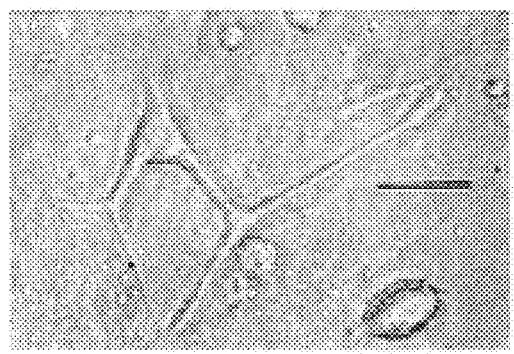

The mouse ES cell line, ES-D3, is obtained from the American Type Culture Collection (ATCC, Manassas, Va.) and maintained with the methods as previously described (Smith, 1991). Briefly, ES-D3 cells are cultured in Dulbecco's modified Eagle's medium (DMEM) on mitotically inactive mouse embryonic fibroblast feeder cells (ATCC, Manassas, Va.). The medium is supplemented with 15% fetal bovine serum, 0.1 mM $\beta$-mercaptoethanol (Sigma, St. Louis, Mo.), and $10^3$ units/ml of leukemia inhibitory factor (LIF) conditioned medium (BRL, Gaithersburg, Md.) to suppress differentiation. To initiate differentiations, ES cells are dispersed with trypsin and resuspended in the medium without supplemental LIF and cultured with the hanging drops (approximate 400 cells per 20 $\mu$l) method for 5 days. Then they are seeded into 100-mm cell culture dishes for another 5 to 7 days, as shown by FIG. 6A. Beating cardiomyocyte clusters are dissected by use of a sterile micropipette (Klung et al., 1995) and re-cultured for another 2 to 3 days (as shown by FIG. 6B) at 37° C. in a humidified atmosphere with 5% $CO_2$. FIG. 6B also shows the morphology of representative spontaneously beating cells having a rate of ~150 beats/min at 37° C. Finally, cultured cells are trypsinized and collected by centrifugation at 500 g for 5-min at room temperature. Collected cells are resuspended in the culture medium with a concentration of $10^6$ cells/ml and ready for the use of cell transplantation.

2. Transfection

Embryonic stem cells are transfected with cloned human VEGF cDNA (phVEGF$_{165}$, a gift from Dr. Kenneth Walsh's laboratory) by a calcium phosphate precipitation method. VEGF cDNA clone (10 $\mu$g) is added to a test tube containing 0.36 ml of HBS (2x) solution (in mM: 274 NaCl, 40 HEPES, 12 dextrose, 10 KCl, 1.4 Na2HPO4, pH 7.05). The calcium concentration of the cDNA solution is brought up to 250 mM by addition of 1 M $CaCl_2$. The cDNA solution is then mixed and incubated at 22° C. for 20 min. After all these procedures, the cDNA solution is dripped over a cell culture (30 to 50% confluence) containing 7 ml of DMEM in a TI-25 flask. The transfection is satisfactory under these conditions. Transfected cells are incubated at 37° C. in air with 5% CO2 added and 98% relative humidity for 3 days. These cells expressing VEGF are ready for intramyocardial transplantation in myocardial infarcted animals.

3. Animal model of MI and ES cell transplantation

The experiments were performed in male Wistar rats (Charles River, Wilmington, Mass.) with an initial body weight of 250–300 g. MI in rats is induced by ligation of the left anterior descending coronary artery under anesthesia with pentobarbital (60 mg/kg, i.p.) in rats using the method described previously (Min et al., 1999). Cell transplantation was performed at the time of induction of MI. In cell transplanted MI rats. ES cell suspension (30 $\mu$l) was separately injected into 3 different sites of myocardium; one within the infarcted area and two at the border between normal and infarcted areas. Each injection contained 10 $\mu$l of the medium with beating ES cells ($10^6$ cells/ml). Control animals receive the same MI operation, but are only injected with the same volume of the cell-free medium. The sham group underwent an identical surgery with neither ligation of the coronary artery nor cell transplantation. Cyclosporine (15 mg/kg/day) will be administrated intraperitoneally throughout the study to all groups.

4. Measurements of hemodynamics and isometric contraction

Different time periods after operation, hemodynamic measurements in vivo are performed with the methods described previously (Litwin et al., 1996). After the final measurement of the study, the heart is rapidly excised. Left ventricular papillary muscle strips are then carefully dissected and vertically connected to a strain-gauge tension transducer (Model MBI 341, Sensotec, Columbus, Ohio). isometric contraction of the papillary muscles obtained from ischemic area are elicited at 35° C. in a 50-ml tissue bath containing the modified Krebs-Henseleit solution by a punctate platinum electrode with square-wave pulses of 5 ms duration at 0.33 Hz. After a 30-min equilibration, the muscle strip is carefully stretched to the length at which maximal tension developed (Lmax). Developed tension (tension produced by the stimulated muscle) is recorded from each muscle at this maximal length. After baseline parameters are obtained, the steady-state response to step-wise increase in bath $Ca^{2+}$ concentrations (1.0, 2.0, 3.0, 4.0 mM) is determined at the plateau of the $Ca^{2+}$-induced inotropic effects. The bath solution is then replaced with fresh modified Krebs-Henseleit solution. Isoproterenol ($10^{-7}$, $10^6$, $10^{-5}$, $10^{-4}$ M) is added cumulatively to determine the isotropic response to $\beta$-adrenergic stimulation. After removal of the papillary muscles for the contractility study, the weight of the left ventricle including the septum is weighed and normalized by body weight. The ratio is calculated as indices of hypertrophy.

5. Measurement of infarct size

MI is restricted to the left ventricle and is transmural in all operated rat hearts. The size of infarct area is quantified according to a classical and well described method (Leenen et al., 1995).

6. Echocardiographic studies

At different time periods after MI or sham operation, the rats are anesthetized again. The echocardiographic procedure is performed by a method as described previously (Litwin et al., 1995; 1996). A commercially available echocardiographic system equipped with a 12-MHz phased-array transducer (Hewlett-Packard) is used for all studies. Left ventricular (LV) mass is calculated using a standard cube formula.. Relative anterior wall thickness and relative posterior wall thickness, LV internal dimensions, endocardial fractional shortening and midwall fractional shortening are measured from at least three consecutive cardiac cycles on a M-mode strip chart recording.

7. Histologic studies

Subsets of animals are sacrificed 6 or 32 weeks after the MI operation. After quickly removing the hearts, the free wall of the left ventricle including the infarcted and periinfarcted regions is embedded in tissue freezing medium (Fisher Scientific, Fair Lawn, N.J.). Frozen tissues are sectioned to 10-$\mu$m slides, and then stained with hematoxylin and eosin. To identify regenerated myocytes from engrafted ES cells, an immunofluorescent method was used to identify the $\alpha$-actin muscle isoform, which is present in fetal cardiomyocytes, but not in normal adult myocytes. Frozen tissue sections are fixed in acetone (4° C.) for 10 min and incubated with a monoclonal anti-$\alpha$-actin antibody (Sigma, St. Louis. Mo.) for 45 min at room temperature. Sections are washed three times in PBS and incubated with Cy3-conjugated goat anti-mouse IgG (1:400 dilution) (Sigma, St. Louis, Mo.) for 45 min at room temperature. After extensive washing in PBS, slides are mounted with DAPI/Antifade (Oncor, Gaithersburg, Md.). New cardiomyocytes from engrafted cells will be verified with several specific markers, such as the antibodies against cardiac myosin, troponin, and actinin (Maltsev et al., 1994; Metzger et al., 1996; Makino et al., 1999).

8. Data analysis

Each experimental group (treated or untreated) comprises at least 6 individual animals. All values are presented as means ±SE. Data are evaluated by one way ANOVA with repeated measurements. Results between two individual groups are compared by using unpaired Student's t-test. Differences between control and treated groups less than $P<0.05$ are considered statistically significant.

EXPERIMENTS AND EMPIRICAL RESULTS

1. Improvement of left ventricular Function after ES cell transplantation

Myocardial infarction (MI) in rats was induced by ligation of the left anterior descending coronary artery. Three groups of rats were used in our experiments. A sham-operated group had the same operation with neither ligation of the coronary artery nor intra-myocardial injection. Treated rats were injected with the medium containing beating ES cells ($10^6$ cells/ml) into infarcted myocardium at three different sites (10 $\mu$l per site). A control group was injected with an equivalent volume of the cell-free culture medium. Six weeks after myocardial infarction, the left ventricular (LV) weight and the ratio of LV weight over body weight were significantly increased in medium-injected animals (n=6, Table 1) compared to sham-operated rats (n=6). However, intramyocardial transplantation of ES cells in MI rats (n=7) significantly decreased the degree of LV hypertrophy and the size of infarcted area (Table 1). The infarcted area was 41±3% for MI rats injected with the culture medium. Intramyocardial transplantation of ES cells reduced the infarcted area to 35±2% (P<0.05). These results suggest that reduction of infarct area may result from improvement of blood supplies and regeneration of new myocardium by transplanted ES cells.

TABLE 1

General characteristics of sham-operated and MI rats

| | Sham (n = 6) | MI + Medium (n = 6) | MI + ES Cells (n = 7) |
|---|---|---|---|
| BW (g) | 433.6 ± 21.4 | 424.7 ± 20.8 | 402.8 ± 18.4 |
| LVW (mg) | 748.4 ± 21.5 | 1005.2 ± 42.3* | 794.6 ± 22.5# |
| LVW/BW (mg/g) | 1.6 ± 0.2 | 2.4 ± 0.3* | 1.8 ± 0.2# |
| Infarcted area (%) | | 41 ± 3 | 35 ± 2# |

Values are means ± SE. Sham, sham-operated rats; MI + Medium, postinfarcted rats injected with cell-free medium; MI + ES Cells, postinfarcted rats with ES cell transplantation. at 6 week after operation. BW: body weight; LVW: left ventricular weight; LVW/BW: ratio of left ventricular weight and body weight. Measurements were conducted at the time after 6 weeks of MI operation. *, P < 0.05; **, P < 0.01; vs. Sham. #, P < 0.05; vs. MI + Medium.

With hemodynamic measurements, the observed data showed that animals injected with the medium exhibited a slower velocity to reach the peak of LV systolic pressure (+dP/dt), a lower LV systolic pressure (LVP), and a higher LV end-diastolic pressure (LVEDP) than those in sham-operated rats. This data is shown by Table 2 and FIG. 1. Six weeks after transplantation of ES cells, cardiac contractility reflected by +dP/dt and LVSP were significantly improved. These data indicate that while the underlying mechanism of improvement of cardiac function by engrafted ES cells remains as yet unknown, nevertheless, it is unequivocal that ES cell transplantation increases the left ventricular performance in MI animals.

TABLE 2

Improvement of left ventricular function after transplantation of ES cells

| | Sham (n = 6) | MI + Medium (n = 6) | MI + ES Cells (n = 7) |
|---|---|---|---|
| LVSP (mmHg) | 138.4 ± 6.3 | 84.6 ± 5.2** | 103.5 ± 7.4*# |
| LVEDP(mmHg) | 10.2 ± 0.9 | 21.7 ± 1.8** | 14.4 ± 1.5*# |
| +dP/dt (mmHg/s × $10^3$) | 8.5 ± 0.7 | 5.6 ± 0.5** | 7.3 ± 0.6# |

Values are means ± SE. Sham, sham-operated rats; MI + Medium, postinfarcted rats injected with cell-free medium; MI + ES Cells, postinfarcted rats transplanted with ES cells. LVSP: the left ventricular systolic pressure; LVEDP: the left ventricular end-diastolic pressure; +dP/dt, the rate of peak left ventricular systolicpressure raise. Measurements were carried out at the time after 6 weeks of MI operation. *, P < 0.05; **, P < 0.01; vs. Sham. #, P < 0.05; vs. MI + Medium.

FIG. 1 illustrates the improvement of left ventricular function after ES cell transplantation using continuous chart strip recordings of hemodynamic measurement in anesthetized animals. Column A represents the sham-operated rat; Column B represents the postinfarcted rat injected with the cell-free medium; and Column C represents the postinfarcted rat transplanted with ES cells). Measurement was conducted 6 weeks after the MI operation. LVP, left ventricular pressure; dP/dt, instant change of left ventricular pressure over instant time.

In vivo, 2-dimensional targeted M-mode echocardiographic assessments were obtained in sham-operated and MI rats and are summarized by Table 2. Echocardiographic studies showed significant differences in LV geometry between rats with MI and sham-operated rats. LV relative anterior wall thickness and relative posterior wall thickness were comparable in sham-operated rats and MI rats with injection medium at 6 weeks after operation. LV dimension enlarged in the infarcted hearts with injection medium after 6 weeks in either systole or diastole. The prominent increase in cavity dimensions in the infarcted hearts from MI control group resulted in a significant decrease in relative anterior wall thickness and relative posterior wall thickness. Both endocardial fractional shortening and midwall fractional shortening were depressed in MI control rats compared to age-matched sham animals. ES cell transplantation significantly blunted the development of the left-ventricular remodeling with a lower LV/body weight ratio than that in MI rats injected with medium that is similar as our in vitro measured data. LV relative anterior wall thickness and LV relative posterior wall thickness were increased in MI rats with ES cell transplantation. Likewise, at the end of experiment, LV diastolic dimension and systolic dimension were reduced in MI rats with ES cell transplantation compared to MI rats injected just with medium. The parallel changes in relative wall thickness and cavity diameter resulted in improvement of cardiac systolic function. Again, the results show that ES cell transplantation improves cardiac function in MI animals.

Figure 2:
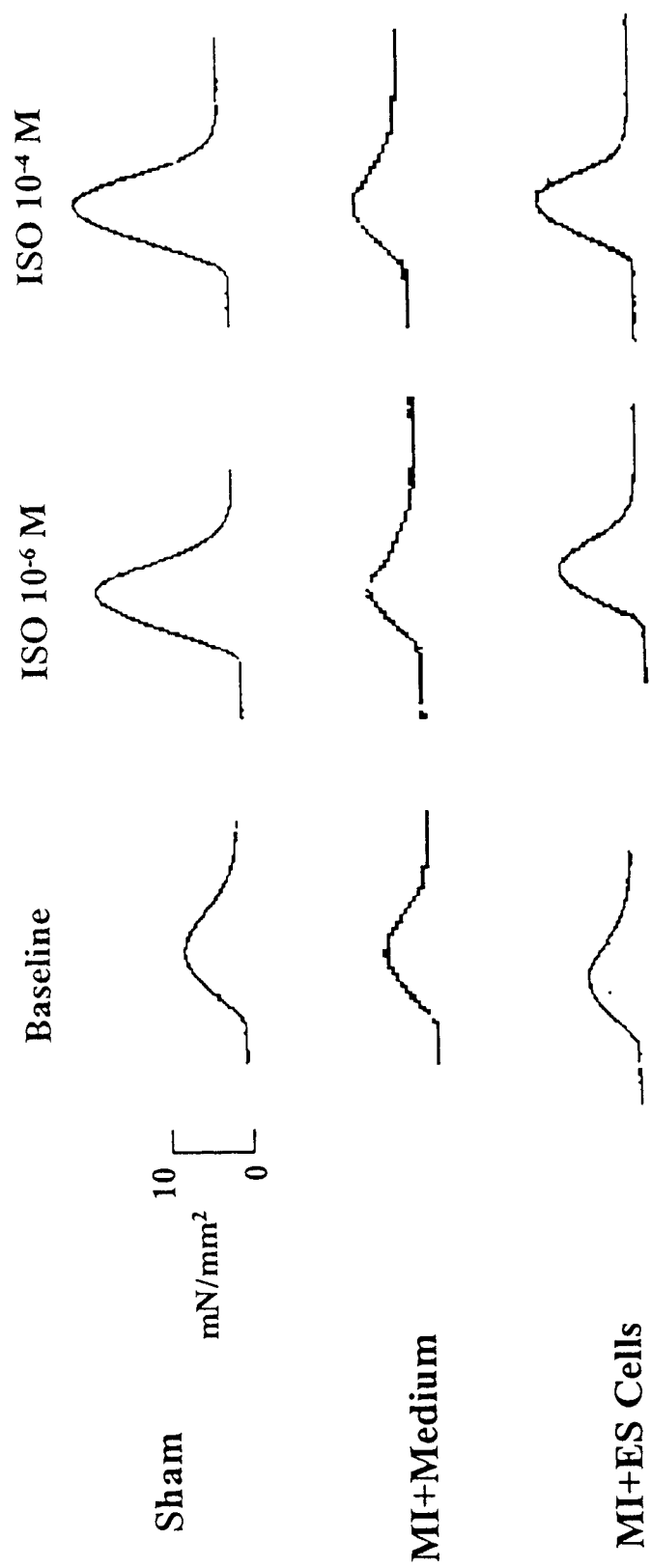
FIG. 2 is a representation of original recordings illustrating improvement of the inotropic effects of isoproterenol on papillary muscles after ES cell transplantation.
Figure 3:
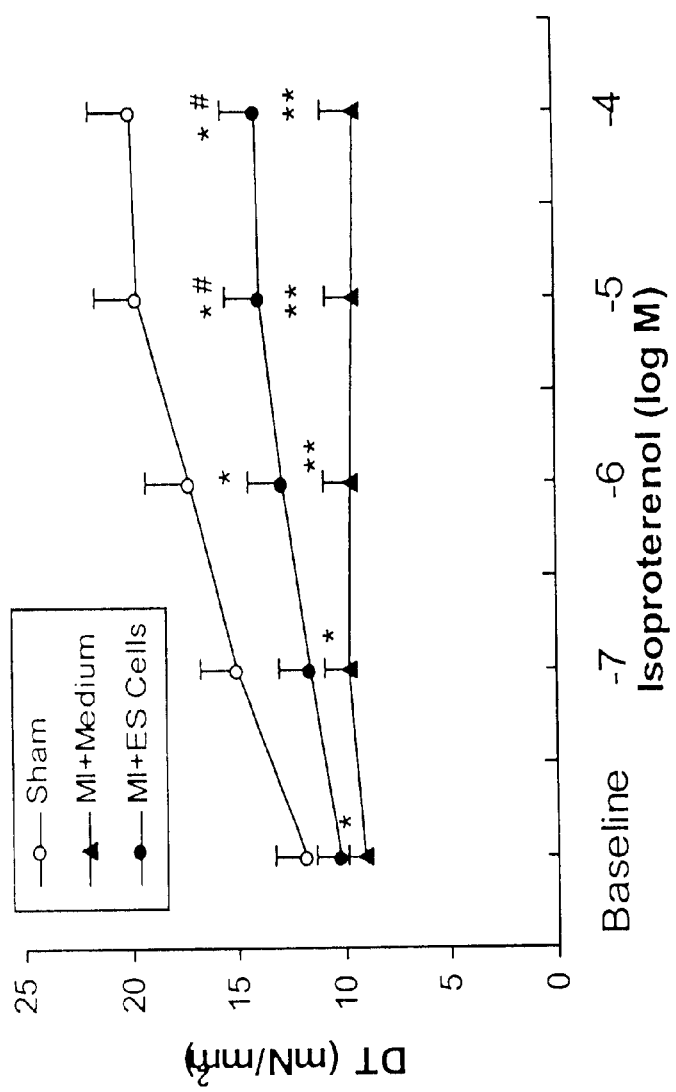
FIG. 3 is a graph illustrating the inotropic response to isoproterenol stimulation after ES cell transplantation.

2. Improvement of isometric contractility in papillary muscle after ES cell transplantation At baseline, papillary muscles isolated from ischemic area in the cell-free medium injected MI group exhibited a significant reduction of developed tension (DT). In animals with intramyocardial injection of ES cells, DT appeared to be significantly preserved. Beta-adrenergic stimulation with cumulative concentrations of isoproterenol (ISO) induced a pronounced increase in DT in normal papillary muscles from sham-operated rats. This is shown by FIG. 2 & FIG. 3 respectively. In contrast, the papillary muscles isolated from MI rats injected with the medium had no positive inotropic response to increase extracellular $Ca^{2+}$ in a concentration-dependent manner. However, the concentration-response curve for the MI rats injected with the medium was significantly shifted downwardly. The curve for the muscle tension versus concentration of extracellular $Ca^{2+}$ in MI rats with ES cell transplantation was in the middle for those for the sham-operated and control MI rats (data not shown). Whereas the exact underlying basis of the improvement remains undetermined, the increase in papillary muscle contractility of MI animals after ES cell transplantation clearly results from the effects of angiogenesis and cardiogenesis by transplanted cells, which in turn enhances or improves whole heart function.

TABLE 3

Echocardiographic measurements of left ventricular function in vivo

|  | Sham | MI + Medium | MI + ES Cells |
| --- | --- | --- | --- |
| PW th (%) | 72.4 ± 21 | 41.6 ± 14* | 61.3 ± 8# |
| AW th (%) | 65.2 ± 8 | 40.7 ± 10# | 57.8 ± 9# |
| LVDd (mm) | 7.3 ± 0.4 | 10.0 ± 0.9** | 8.2 ± 0.3# |
| LVDs (mm) | 4.6 ± 0.4 | 7.5 ± 1.1** | 5.8 ± 0.7 |
| En FS (%) | 36.8 ± 5.4 | 21.0 ± 2.6** | 30.7 ± 4.3# |
| MW FS (%) | 20.6 ± 3.6 | 13.3 ± 1.8* | 17.8 ± 2.6# |

TABLE 3-continued

Echocardiographic measurements of left ventricular function in vivo

|  | Sham | MI + Medium | MI + ES Cells |
| --- | --- | --- | --- |
| LV Mass (g) | 0.65 ± 0.1 | 1.10 ± 0.2** | 0.81 ± 0.2# |
| LV Mass/BW (mg/g) | 1.4 ± 0.2 | 2.4 ± 0.2** | 1.7 ± 0.4# |

Values are means ± SE. Each group has 5 rats. PW th, relative posterior wall thickness; AW th, relative anterior wall thickness; LVDd, left ventricular diastolic dimension; LVDs, left ventricular systolic dimension; En FS, endocardial fractional shortening; MW FS, midwall fractional shortening; LV Mass/BW, ratio of left mass and body weight. *, $P < 0.05$; **, $P < 0.01$; vs. Sham. #, $P < 0.05$; vs. MI + Medium.

FIG. 2 shows the improvement of the inotropic effects of isoproterenol on papillary muscles after ES cell transplantation. FIG. 2 constitutes original representative recordings which show inotropic responsiveness during isoproterenol stimulation in papillary muscles isolated from a sham-operated rat (Sham),; and from a postinfarcted rat injected with the cell-free medium (MI+Medium); and from a postinfarcted rat transplanted with ES cells (MI+ES cells). The experiments were carried out 6 weeks after the MI operation.

FIG. 3 illustrates the inotropic response to isoproterenol stimulation after ES cell transplantation. The effects of different extracellular isoproterenol concentrations on developed tension of isolated papillary muscles are shown in sham-operated and MI rats 6 weeks after the MI operation. As seen in FIG. 3, Sham represents the sham-operated group (n=6); MI+Medium represents the MI group injected with cell-free medium (n=6); MI+ES Cells represents the MI group transplanted with ES cells (n=7). DT is the developed tension produced by the stimulated muscle. * is $P<0.05$; **, is $P<0.01$, vs. Sham; and $^{\#}$ is $P<0.05$, vs. MI+Medium.

3. Histology and Immunofluoresent Studies

Figure 4:
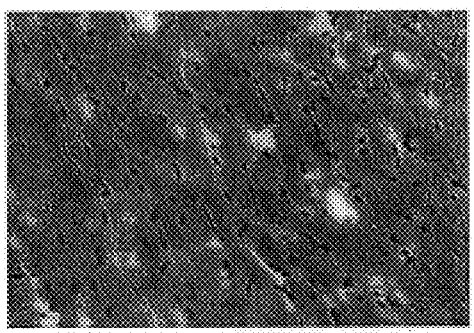
FIGS. 4A–4D are hematoxylin-eosin stained histological sections viewed with light microscopy showing engrafted cells in the infarcted myocardium of MI rats.
Figure 4:
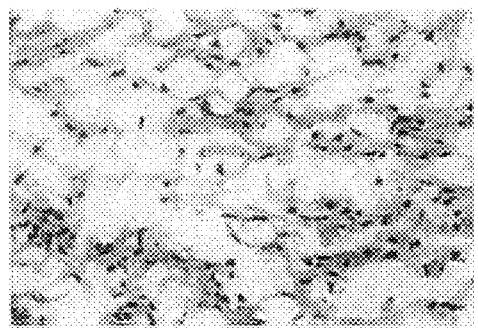
Figure 4:
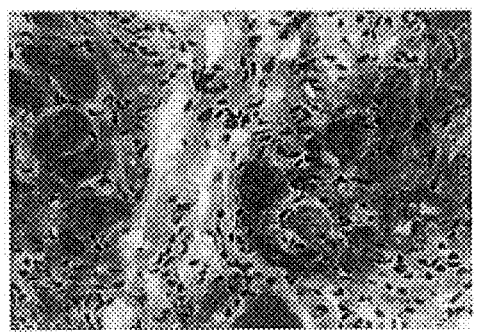
Figure 4:
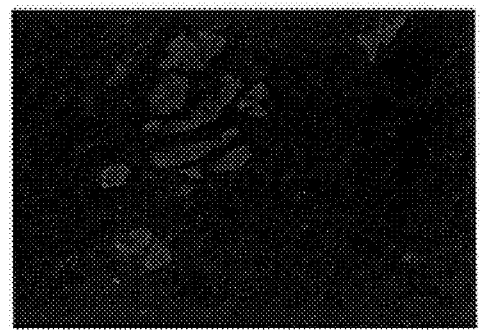

The survey of hematoxylin-eosin-stained sections with light microscopy is illustrated by FIGS. 4A–4D respectively. FIG. 4A represents the sham operated myocardium. In comparison, FIG. 4B shows the typical fibrosis in the medium-injected MI rats 6 weeks after the operation. Also, in cell transplanted MI rats characteristic phenotype of engrafted ES cells were found in infarcted areas as shown by FIG. 4C. Immunofluoresent techniques were applied and confirmed that these cells were clearly distinct from both normal myocytes and infarcted tissue. The viability of the implanted ES cells was also demonstrated by the strong positive staining to cytoplasmic α-actin as shown by FIG. 4D, which is rarely seen in adult rat myocardium (Leor et al., 1996; Scorsin et al., 1996). In addition, α-actin staining was negative in myocardium of the sham-operated and medium-injected MI hearts. These results demonstrate that engrafted ES Cells can survive in infarcted myocardium and cardiogenesis actually occurred in infarct hearts.

4. Transplantation of ES cells transfected with VEGF into infarcted myocardium

In some experiments, the feasibility of transplanting ES cells—with or without transfection of a vascular endothelial growth factor (phVEGF$_{165}$)—into infarcted myocardium in mice was investigated. Cardiac function was evaluated in mice with or without ES cell transplantation after ligation of the left anterior descending coronary artery. Treated mice were injected with the medium containing beating ES cells ($10^6$ cells/ml) into infarcted myocardium at three different sites (10 μl per site). control group was injected with an equivalent volume of the culture medium. The sham group had the same operation with neither ligation of the coronary artery not intra-myocardial injection. Six weeks after myocardial infarction, the systolic pressure and the velocity to the maximal pressure of the left ventricle in ES cell-transplanted mice were significantly greater than those in MI mice injected with the cell-free medium only. Transplantation of ES cells with overexpression of VEGF improved left ventricular function even greater. Immunofluorescent staining showed a significant overexpression of VEGF in transfected ES cells. The results are summarized by FIG. 5. The empirical data showed that ES cell transplantation significantly improved myocardial function in infarcted mice, and that the degree of improvement was even greater with ES cells overexpressing VEGF.

Figure 5:
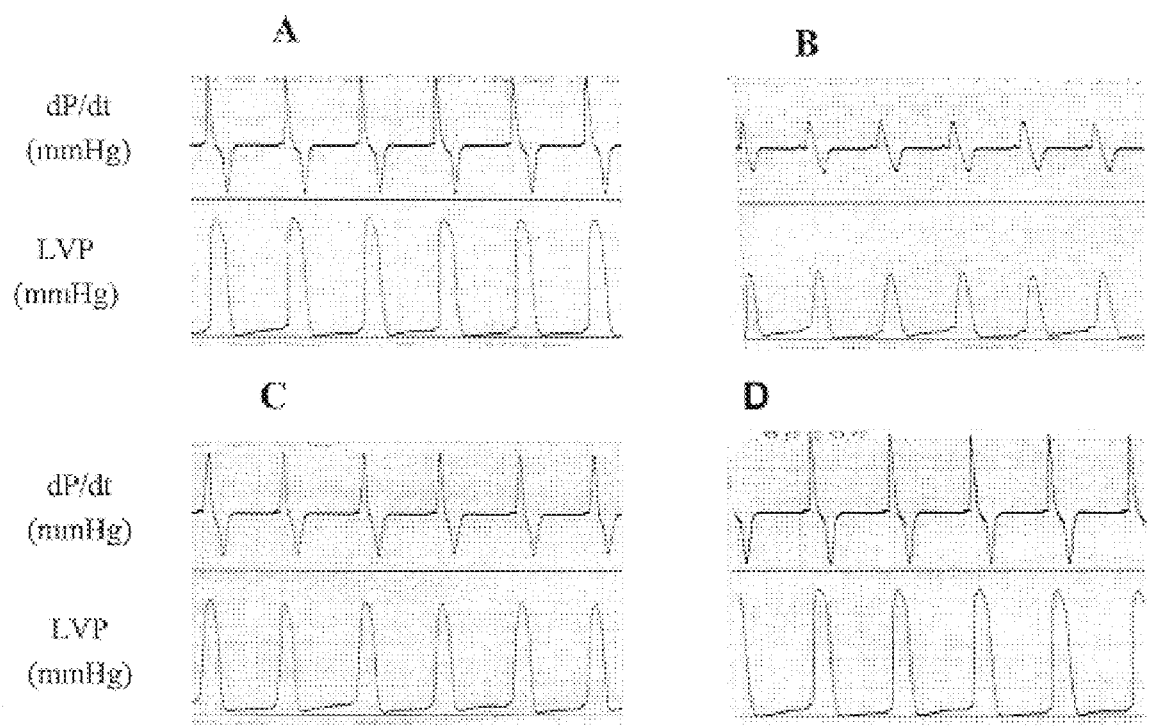
FIGS. 5A–5D are representations of continuous chart strip recordings of hemodynamic measurements in anesthetized animals illustrating the improvement of ventricular contractility after ES cell transplantation in MI mice.

FIG. 5 illustrates the improvement of ventricular contractility after ES cell transplantation in MI mice as continuous chart strip recordings of hemodynamic measurement in anesthetized animals. FIG. 5A represents the sham-operated mouse; FIG. 5B represents the postinfarcted mouse injected with the cell-free medium; FIG. 5C represents the postinfarcted mouse transplanted with ES cells; and FIG. 5D represents the postinfarcted mouse transplanted with ES cells overexpressing VEGF. Measurements were conducted 6 weeks after the MI operation. LVP, left ventricular pressure; dP/dt, instant change of left ventricular pressure over instant time.

SUMMARY OF EMPIRICAL RESULTS

Our recent study demonstrates that transplanted embryonic stem (ES) cells survive in infarcted myocardium and improve cardiac function in postinfarcted rats. This study was designed to investigate the feasibility of transplantation of ES cells with or without transfection of a vascular endothelial growth factor ($phVEGF_{165}$) into infarcted myocardium in mice. Myocardial infarction (MI) in mice was developed by ligation of the left anterior descending coronary. Cardiac function was evaluated in mice with or without ES cell transplantation. Treated mice were injected with the medium containing beating ES cells ($10^6$ cells/ml) into infarcted myocardium at three different sites (10 µl per site). Control group was injected with an equivalent volume of the culture medium. The sham group had the same operation with neither ligation of the coronary artery nor intra-myocardial injection. Six weeks after myocardial infarction, the systolic pressure and the velocity to the maximal pressure of the left ventricle in ES cell-transplanted mice were significantly greater than those in MI mice injected with the medium only. Isometric contraction of left ventricular papillary muscles was significantly improved in ES cell-transplanted mice than in MI mice treated with the medium only. The response of papillary muscles to isoproterenol (ISO) was significantly preserved in ES cell-transplanted mice, whereas the ISO-induced inotropic effect was severely blunted in the medium-injected mice. The effects of transplantation of ES cells transfected with VEGF on the improvement of left ventricular function and papillary muscle contractility was even grater. Western blotting analysis demonstrated the overexpression of VEGF protein in implanted area Histological study in ES cell-transplanted mice after 6–8 weeks of the MI operation showed that ES cells were surviving in infarcted myocardium. Furthermore, immunofluorescent staining showed a significant overexpression of VEGF in grafted ES cells in implanted areas. We concluded that ES cell transplantation significantly improved myocardial function in infarcted mice, and that the improvement was even greater with ES cells overexpressing VEGF.

LITERATURE CITED

1. Bloom F E. Breakthroughs 1999 (editorial). *Science* 1999; 286: 2267.

2. Bishop S P, Anderson P G, Tucker D C. Morphological development of the rat heart growing in oculo in the absence of hemodynamic work load. *Circ Res.* 1990; 66: 84–102.

3. Bradley A. Cell differentiation. *Current Opinion in Cell Biology* 1990; 2: 1013–1017.

4. Chiu R C J, Zibaitis A, Kao R L. Cellular cardiomyoplasty: myocardial regeneration with satellite cell implantation. *Ann Thorac Surg.* 1995;60: 12–18.

5. Cittadini A, Grossman J D. Napoli R, et al. Growth hormone attenuates early left ventricular remodeling and improves cardiac function in rats with large myocardial infarction. *J Am Coll Cardiol.* 1997;29: 1109–1116.

6. Eriksson H. Heart failure: a growing public health problem. *J Inter Med.* 1995;237: 135–141.

7. Hescheler J, Fleishmann B K, Lentini S, et al. Embryonic stem cell: a model to study structural and functional properties in cardiomyocytes. *Cardiovas Res.* 1997; 36: 149–162.

8. Kim S S and Vacanti J P. The current status of tissue engineering as potential therapy. *Semin Pediatr Surg* 1999: 8: 119–123.

9. Kilborn M J, Fedida D. A study of the developmental changes in outward currents of rat ventricular myocytes. *J Physiol Lon.* 1990;430: 37–60.

10. Klung M G, Soonpaa M H, Field L J. DNA synthesis and multinucleation in embryonic stem cell-derived cardiomyocytes. *Am J Physiol.* 1995;269: H1913–H1921.

11. Klung M G, Soonpaa M H, Koh G Y and Field L J. Genetically selected cardiomyocytes from differentiating embryonic stem cells form stable intracardiac grates. *J Clin Invest* 1996; 98: 216–224.

12. Koh G Y, Klung M G, Soonpaa M H, et al. Long-term survival of AT1 cardiomyocyte grafts in syngeneic myocardium. *Am J Physiol.* 1993:264: H1727–H1733.

13. Lavranos T C, Rathjen P D and Seamark R F. Trophic effects of myeloid leukaemia inhibitory factor (LIF) on mouse embryos. *J Reprod Fertil* 1995; 105: 331–338.

14. Leenen F H H, Huang B S, Yu H, et al. Brain "Quabain" mediates sympathetic hyperactivity in congestive heart failure. *Circ Res.* 1995;77: 993–1000.

15. Leor J, Patterson M, Quinones M J et al. Transplantation of fetal myocardial tissue into the infarcted myocardium of rat: a potential method for repair of infarcted myocardium. *Circulation.* 1996;94(Suppl II): II332–II336.

16. Leor J, Prentice H, Sartorelli V, et al. Gene transfer and cell transplantation: an experimental approach to repair a "broken heart". *Cardiovasc Res.* 1997;35: 431–441.

17. Li R K, Jia Z Q. Weisel R D, et al. Cardiomyocyte transplantation improves heart function. *Ann Thorac Surg.* 1996;62: 654–661.

18. Li R K, Mickle D A G, Weisel R D, et al. In vivo survival and function of transplanted rat cardiomyocytes. *Circ. Res.* 1996;78: 283–288.

19. Li R K, Mickle D A G, Weisel R D, et al. Natural history of fetal rat cardiomyocytes transplanted into adult rat myocardial scar tissue. *Circulation* 1997;96(Suppl II): II179–II187.

20. Li R K, Weisel R D, Mickle D A, et al. Autologous porcine heart cell transplantation improved heart function after a myocardial infarction, *J Thorac Cardiovasc Surg.* 2000; 119: 62–68.

21. Litwin S E, Katz S E, Weinber E O, et al. Serial echocardiographic-Doppler assessment of left ventricular geometry and function in rats with pressure-overload hypertrophy: chronic angiotensin-converting enzyme inhibition attenuates the transition to heart failure. *Circulation* 1995;91: 2642–2654.

22. Litwin S E, Katz S E, Morgan J P, et al. Long-term captopril treatment improves diastolic filling more than systolic performance in arts with large myocardial infarction. *J Am Coll Cardiol* 1996; 28: 773–781.

23. Losordo D W, Vale P R, Symes J F., et al. Gene therapy for myocardial angiogenesis-Initial clinical results with direct myocardial injection of phVEGF$_{165}$ as sole therapy for myocardial ischemia. *Circulation* 1998; 98: 2800–2804.

24. Makino S, Fukuda K, Miyoshi S, et al. Cardiomyocytes can be generated from marrow stromal cells in vitrol *J Clin Invest* 1999; 103: 697–705.

25. Maltsev V A, Rohwedel J, Hescheler J and Wobus A M. Embryonic stem cells differentiate in vitro into cardiomyocytes representing sinusnodal, atrial and ventricular cell types. *Mech Dev* 1993; 191: 42–50.

26. Maltsev V A, Wobus A M, Rohwedel J, Bader M and Hescheler J. Cardiomyocytes differentiated in vitro from embryonic stem cells developmentally express cardiac-specific genes and ionic currents. *Circ Res* 1994; 75: 233–244.

27. Metzger J M, Lin W-I and Samuelson L C. Transition in cardiac contractile sensitivity to calcium during the in vitro differentiation of mouse embryonic stem cells. *J Cell Biol* 1994; 126: 701–711.

28. Metzger J M, Lin W-I and Samuelson L C. Vital staining of cardiac myocytes during embryonic stem cells cardiogenesis in vitro. *Circ Res* 1996; 78: 547–552.

29. Midha R, Mackinnon S E, Wade J A, et al. Chronic cyclosporine A therapy in rats. *Microsurgery.* 1992; 13: 273–276.

30. Min J Y, Sandmann S, Meissner A, et al. Differential effects of mibefradil, verapamil, and amlodipine on myocardial function and intracellular $Ca^{2+}$ handling in rats with chronic myocardial infarction. *J Pharmacol Exp Ther.* 1999; 291: 1038–1044.

31. Min J Y, Yang Y K, Wang J F, Morgan J P and Xiao Y-F. Embryonic stem cells transplantation improves cardiac function in post-infarcted heart failure. *J Heart Failure* 2000a; 6(3): 1. *Young Investigator Award.*

32. Min J Y, Yang Y K, Liu L X, Morgan J P and Xiao Y-F. Improvement of heart function in postinfarcted rats by transplantation of embryonic stem cells. *Circulation* Abstract for the 73$^{rd}$ AHA meeting, 2000b. *Young Investigator Award.*

33. Min J Y, Hampton T G, Wang J F, DeAngells J, and Morgan J P. Depressed tolerance to fluoraocarbon-simulated ischemia in failing myocardium due to impaired $[Ca^{2+}]_i$ modulation. *Am J Physiol (Heart Circ Physiol)* 2000c; 279: H35–H46.

34. Pfeffier J M, Pfeffer M A, Branuwald E. Influence of chronic capatopril therapy on the infarcted left ventricle of the rat. *Circ Res.* 1985;57: 84–95.

35. Rathjen P D, Whyatt J L L M, Rathjen B J. Properties and uses of embryonic stem cells: prospects for application to human biology and gene therapy. *Reprod Fertil Dev.* 1998;10: 31–47.

36. Robbins J, Doetschman T, Jones W K, et al. Embryonic stem cells as a model for cardiogenesis. *Trends Cardiovasc Med.* 1992;2: 44–50.

37. Scorsin M, Marotte F, Sabri A, et al. Can grafted cardiomyocytes colonize periinfarction myocardial areas? *circulation* 1996; 94(Suppl II): II337–II340.

38. Scorsin M, Hagege A, Vilquin J T, et al. Comparison of the effects of fetal cardiomyocyte and skeletal myoblast transplantation on post infarction left ventricular function. *J Thorac Cardiovasc Surg.* 2000; 119: 1169–1175.

39. Shamblott M J, et al. Derivation of pluripotent stem cells from cultured human primordial germ cells. *Proc Natl Acad Sci USA* 1998; 95: 13726–13731.

40. Smith A G. Culture and differentiation of embryonic stem cells. *J Tissue Culture Methods.* 1991;13: 89–94.

41. Soonpaa M H, Koh G Y, Klug M G, et al. Formation of nascent intercalated disks between grafted fetal cardiomyocytes and host myocardium. *Science.* 1994;264: 98–101.

42. Tavazzi I. Epidemiological burden of heart failure. *Heart* 1998; 79(Suppl 2): S6–9. Thomson J A, et al. Embryonic stem cell lines derived from human blastocytsts. *Science.* 1998; 282: 114598–1147.

43. Tomita S, Li R K, Weisel R D, et al. Autologous transplantation of bone marrow cells improves damaged heart function. *Circulation.* 1999;100(Suppl II): II247–II256.

44. Van Meter C H, Claycomb W C, Delcarpio J B, et al. Myoblast transplantation in the porcine model; A potential technique for myocardial repair. *J Thorac Cardiovasc Surg.* 1995; 110: 1142–1148.

45. Watanabe E, Smith, D M Jr., Delcarpio J B., et al. Cardiomyocyte transplantation in a porcine myocardial infarction model. *Cell Transplantation* 1998; 7: 239–246.

46. Westfall M V, Pasyk K A, Yule D I, Samuelson L C and Metzger J M. Ultrastructure and cell-cell coupling of cardiac myocytes differentiating in embryonic stem cell cultures. *Cell Motil Cytoskeleton* 1997; 36: 43–54.

47. Yank Y K, Min J Y, Morgan J P and Xiao Y F. Transplantation of embryonic stem cells overexpressing vascular endothelial growth factor into infarcted myocardium in mice. *Circulation* Abstract for the 73$^{rd}$ AHA meeting, 2000.

48. Zhang J P, Blum M G, Chang A C, Yu Shyr, Blair K S A, Pierson III R N. Immunohistologic evaluation of the mechanisms of mediated hyperacute lung rejection, and the effect of treatment with K76-COOH, FUT-175 and anti-Gal column immunoabsorption. *Xenotransplantation* 1999; 6: 249–61.

What we claim is:

1. A method for improving cardiac function in a mammal after a myocardial infarct, said method comprising the steps of:

maintaining a plurality of undifferentiated, genetically altered mammalian embryonic stem cells in vitro in a culture medium containing at least one selected from the group consisting of leukemia inhibitory factor and fibroblast feeder cells; said undifferentiated, genetically altered mammalian embryonic stem cells comprising:
a mammalian embryonic stem cell which
(i) remains uncommitted and undifferentiated while passed in vitro,
(ii) is implantable in vivo at a chosen anatomic site as an uncommitted cell, and
(iii) engrafts in situ after implantation in a mammal at a local anatomic site, and,
(iv) contains a vector comprising a DNA sequence operably linked to a promoter, wherein the DNA sequence encodes an angiogenic factor which is expressed in situ;

subsequently culturing said undifferentiated, genetically altered mammalian embryonic stem cells for a predetermined time in a culture media in the absence of leukemia inhibitory factor and fibroblast feeder cells to yield a cellular inoculum comprising mammalian cells in which differentiation has been initiated;

introducing said cellular inoculum to at least a portion of the previously infarcted area of the heart tissue; and allowing said introduced cellular inoculum to engraft in situ as viable cells situated within the previously infarcted area of the heart tissue, wherein the engraftment results in improved cardiac function in said mammal.

2. A method for improving cardiac function in a mammal after a myocardial infarct, said method comprising the steps of:

obtaining a plurality of progeny cells of undifferentiated, genetically altered mammalian embryonic stem cells, maintaining said undifferentiated, genetically altered progeny cells in vitro in a culture medium containing at least one selected from the group consisting of leukemia inhibitory factor and fibroblast feeder cells, said undifferentiated, genetically altered progeny cells comprising:

progeny cells of mammalian embryonic stem cells which
(i) remain undifferentiated while passed in vitro,
(ii) are implantable in vivo at a chosen anatomic site as viable cells,
(iii) engraft in situ after implantation in a mammal at a local anatomic site, and,
(iv) contain a vector comprising a DNA sequence operably linked to a promoter, wherein the DNA sequence encodes an angiogenic factor, which is expressed in situ;

subsequently culturing said undifferentiated, genetically altered progeny cells for a predetermined time in a culture media in the absence of leukemia inhibitory factor and fibroblast feeder cells to yield a cellular inoculum comprising mammalian cells in which differentiation has been initiated;

introducing said cellular inoculum to at least a portion of the previously infarcted area of the heart tissue; and allowing said introduced cellular inoculum to engraft in situ as viable cells situated within the previously infarcted area of the heart tissue, wherein the engraftment results in improved cardiac function in said mammal.

3. The method for improving cardiac function as recited in claim 1 or 2, wherein said DNA sequence in said genetically altered mammalian embryonic stem cells is an endogeneous nucleotide sequence.

4. The method for improving cardiac function as recited in claim 1 or 2, wherein said DNA sequence in said genetically altered mammalian embryonic stem cells is a heterologous nucleotide sequence.

5. The method as recited in claims 1 or 2, wherein said DNA sequence encodes an angiogenic factor selected from the group consisting of vascular endothelial growth factor, fibroblast growth factor 1, fibroblast growth factor 2, transforming growth factor $\alpha$, transforming growth factor $\beta_{1-5}$, insulin-like growth factor 1 and insulin-like growth factor 2.

* * * * *